United States Patent
Cho

(10) Patent No.: US 9,089,230 B2
(45) Date of Patent: Jul. 28, 2015

(54) PILLOW HAVING A PLURALITY OF POLYGONAL UNITS

(75) Inventor: Soon Hyung Cho, Goyang-si (KR)

(73) Assignee: VENYGOOD CO., LTD., Gyeonggi-Do (KR)

( * ) Notice: Subject to any disclaimer, the term of this patent is extended or adjusted under 35 U.S.C. 154(b) by 0 days.

(21) Appl. No.: 13/976,777

(22) PCT Filed: May 15, 2012

(86) PCT No.: PCT/KR2012/003778
§ 371 (c)(1),
(2), (4) Date: Jun. 27, 2013

(87) PCT Pub. No.: WO2012/165776
PCT Pub. Date: Dec. 6, 2012

(65) Prior Publication Data
US 2014/0075676 A1    Mar. 20, 2014

(51) Int. Cl.
A47C 20/00    (2006.01)
A47G 9/10     (2006.01)
A61F 5/01     (2006.01)

(52) U.S. Cl.
CPC .. *A47G 9/109* (2013.01); *A61F 5/01* (2013.01)

(58) Field of Classification Search
CPC . A47C 27/00; A47G 9/10; A47G 2009/1018; A47G 9/109
USPC ............ 5/630, 640, 632, 634, 636, 645, 648, 5/657
See application file for complete search history.

(56) References Cited

U.S. PATENT DOCUMENTS

| | | | | |
|---|---|---|---|---|
| 3,736,023 A * | 5/1973 | Lyons | ........................... | 297/118 |
| 3,968,529 A * | 7/1976 | Levin et al. | ....................... | 5/640 |
| 4,171,549 A * | 10/1979 | Morrell et al. | .................... | 5/632 |
| 4,777,678 A * | 10/1988 | Moore | ............................. | 5/657 |
| 4,824,411 A * | 4/1989 | McClanahan | ................. | 441/129 |
| 4,905,330 A * | 3/1990 | Jacobs | ........................... | 5/705 |
| 4,987,625 A * | 1/1991 | Edelson | .......................... | 5/657 |
| 5,086,529 A * | 2/1992 | DeGroot | .......................... | 5/710 |
| 5,163,195 A * | 11/1992 | Hill | ................................ | 5/637 |
| 5,448,790 A * | 9/1995 | Saro et al. | ......................... | 5/657 |
| 5,815,862 A * | 10/1998 | Rygiel | .............................. | 5/632 |

(Continued)

FOREIGN PATENT DOCUMENTS

| | | |
|---|---|---|
| JP | 10-85106 | 4/1998 |
| JP | 2002-360384 | 12/2002 |
| KR | 20-1998-0057241 | 10/1998 |

(Continued)

*Primary Examiner* — Timothy D Collins
*Assistant Examiner* — Richard G Davis
(74) *Attorney, Agent, or Firm* — IPLA P.A.; James E. Bame

(57) ABSTRACT

A pillow having a plurality of polygonal units, includes: a triangular pentahedron unit having a shape of a triangular prism; a one-side inclined square hexahedral unit having a shape of a square pillar; a rectangular hexahedron unit having a shape of a rectangular pillar; a both-side inclined rectangular hexahedron unit having a shape of a rectangular pillar; a rhombic hexahedron unit having a shape of a rhombic pillar; an isosceles-triangular pentahedron unit having a shape of an isosceles triangular prism; and a rectangular panel-shaped hexahedron unit having a shape of a rectangular pillar, whereby the units are sewn together in such a way so as to selectively come into surface contact with each other or be stacked, thus forming one pillow, with the respective units being filled with stuffing.

6 Claims, 11 Drawing Sheets

(56) References Cited

U.S. PATENT DOCUMENTS

| | | | |
|---|---|---|---|
| 5,987,675 A * | 11/1999 | Kim | 5/632 |
| 5,987,676 A * | 11/1999 | Littleford et al. | 5/636 |
| 6,006,380 A | 12/1999 | Sramek | |
| 7,020,918 B1 * | 4/2006 | Tinsley | 5/632 |
| 2008/0271247 A1 * | 11/2008 | Kogan | 5/636 |
| 2012/0144591 A1 * | 6/2012 | Mobley et al. | 5/640 |
| 2013/0014328 A1 * | 1/2013 | Requet et al. | 5/640 |

FOREIGN PATENT DOCUMENTS

| | | |
|---|---|---|
| KR | 20-0248442 | 10/2001 |
| KR | 102010001534 | 2/2010 |
| KR | 10-20100135527 | 12/2010 |
| KR | 10-2011-0012265 | 2/2011 |

* cited by examiner (a)

(b)

PILLOW HAVING A PLURALITY OF POLYGONAL UNITS

BACKGROUND OF THE INVENTION

The present invention relates, in general, to pillows, and more particularly, to a pillow which is formed using a plurality of polygonal units, thus allowing a user to have deep sleep and thereby protecting and correcting the cervical vertebrae.

Generally, it is already known that a bad sleep posture deforms the neck bones and negatively affects the back bone, the waist, and the pelvis.

Thus, if people use a very thin pillow or sleep without a pillow, excessive body pressure is generated on the shoulder and the shoulder blade, so that they have a pain in the shoulder and arm, and shear load is generated on the lumbar, so that most people complain of sharp pains in their backs, and besides, people have a pain in the spine and the muscle of the entire neck becomes stiff.

Further, pressure occurs in an abdominal region, and a person having poor liver function feels seriously uncomfortable. When this continues for a lengthy period of time, the liver function becomes poor. Hence, the pillow supporting the head during a sleep that occupies about a third of a lifetime plays an important role.

However, a conventional cushioning pillow filled with a lot of cotton is problematic in that the head and the shoulder are raised, thus causing wrinkling at the neck, snoring, and pains in the back of the neck, the shoulders and the spine.

Further, since the head and shoulder are raised, the lungs are pressurized and lung function is deteriorated, so that a sufficient amount of oxygen is not supplied. Thereby, a person does not feel completely refreshed even after he or she sleeps. If such a pillow is used for a lengthy period of time, there is high possibility of the neck being deformed into cervical hypolordosis, and the risk of a herniated cervical disc is high.

Therefore, a so-called memory foam pillow or a latex pillow as a pillow manufactured shape memory sponge has been proposed. This pillow is good in texture but is too soft. Thus, the head height of the pillow is proper but the pillow cannot support the cervical vertebrae, so that the height of a pillow portion supporting the cervical vertebrae is undesirably lower than that of a pillow portion supporting the head.

For this reason, it obstructs the blood flow of the back of neck, so that blood is not smoothly supplied to some blood vessels of the brain, and a person has a pain in the shoulder and the spine around the back after he or she sleeps. In addition, this disturbs deep sleep, so that a person feels sluggish even after sleeping, and suffers from a backache. If the pillow is used for a lengthy period of time, the risk of the cervical hypolordosis or the herniated cervical disc becomes high.

Further, a circular pillow or a wood pillow filled with hard pillow chips as stuffing is problematic in that a load concentrates at a specific portion, such as the $4^{th}$ cervical vertebrae or the $5^{th}$ cervical vertebrae, so that the muscles around the neck and the cervical vertebrae are strained and circulation of blood is disturbed when the pillow is used for a lengthy period of time.

In order to solve the above problems, various pillows have been disclosed for supporting the cervical vertebrae: a pillow according to Korean U.M. Registration No. 20-0248442 includes a pillow body and a cervical vertebrae supporting pillow, a pillow according to Korean Patent Laid-Open Publication No. 10-2011-0012265 is configured such that a head support part and a cervical vertebral support part are separated from each other by means of a separator sheet, and a pillow according to Korean Patent No. 10-1021355 is configured such that a plurality of cushioning support members are inserted therein.

However, the pillows according to the prior art are problematic in that it is impossible to disperse the head load, so that it is undesirable.

That is, the pillow according to Korean U.M. Registration No. 20-0248442 is similar to a simple circular pillow, so that a user's head is tilted back when sleeping with the pillow.

Thus, after a user has slept using the pillow, he or she has a tingling pain in the back of neck. All users sleep with their mouths open, so that they feel thirsty, suffer from nightmares, do not have deep sleep, catch cold easily, and frequently suffer from ear, nose and throat diseases.

Further, the pillow of Korean Patent Laid-Open Publication No. 10-2011-0012265 is configured such that, when the head load presses the head support part, the cervical vertebral support part comes into contact with the cervical vertebrae. However, this pillow is problematic in that the separator sheet is present between the head support part and the cervical vertebral support part, so that the cervical vertebral support part cannot reliably come into contact with the cervical vertebrae, and besides, a resilient and soft material should be used as pillow stuffing, so that the pillow cannot reliably support the cervical vertebrae.

Furthermore, the pillow of Korean Patent No. 10-1021355 can adjust only a height, so that it merely functions to separately support the head and the cervical vertebrae. Thus, the pillow is problematic in that it is difficult to properly support the cervical vertebrae of all persons who are different in body size.

CITATION LIST

Patent Literature 1 KR 20-0248442 Y1 2001.10.29
Patent Literature 2 KR 10-2011-0012265 A 2011.02.09
Patent Literature 3 KR 10-1021355 B1 2011.03.16

SUMMARY OF THE INVENTION

Accordingly, the present invention has been made keeping in mind the above problems occurring in the related art, and is intended to provide a pillow having a plurality of polygonal units, which are deformed only at portions contacting the human body while dispersing the load of a head, thus stably supporting the cervical vertebrae and the occipital region.

Another object of the present invention is to provide a pillow, which is improved in contact degree with the human body, thus allowing a user to sleep while keeping the skeleton of the body natural, in addition to correcting the cervical vertebrae.

In an aspect, the present invention provides a pillow having a plurality of polygonal units: including a triangular pentahedron unit having a shape of a triangular prism that is triangular in cross-section; a one-side inclined square hexahedral unit having a shape of a square pillar that is square in cross-section, with a one-side inclined surface thereof being inclined; a rectangular hexahedron unit having a shape of a rectangular pillar that is rectangular in cross-section; a both-side inclined rectangular hexahedron unit having a shape of a rectangular pillar that is rectangular in cross-section, with a both-side inclined surface thereof being inclined; a rhombic hexahedron unit having a shape of a rhombic pillar that is rhombic in cross-section; an isosceles-triangular pentahedron unit having a shape of an isosceles triangular prism that is isosceles triangular in cross-section; and a rectangular panel-shaped hexahedron unit having a shape of a rectangular pillar that is rectangular in cross-section, and having a shape of a rectangular panel, whereby the units are sewn together in such a way so as to selectively come into surface contact with each other or be stacked, thus forming one pillar, with the respective units being filled with stuffing.

Further, in another aspect, the present invention provides a pillow having a plurality of polygonal units: including a cervical vertebral support part, having a bottom dead point part formed by sewing gathered lower corner ends of a plurality of triangular pentahedron units, each of the triangular pentahedron units being filled with stuffing and having a shape of a triangular prism that is triangular in cross-section; an upper dead point part formed by connecting and sewing upper corner ends of a pair of triangular pentahedron units disposed on a middle portion among the plurality of triangular pentahedron units; and a surface of one triangular pentahedron unit protruding to a front of a bottom part, in a wedge shape; and an occipital region support part connected to a rear portion of the cervical vertebral support part, and formed by horizontally connecting the following units: a one-side inclined square hexahedral unit having a shape of a square pillar that is square in cross-section, with a one-side inclined surface thereof being inclined backwards; a rectangular hexahedron unit having a shape of a rectangular pillar that is rectangular in cross-section; another one-side inclined square hexahedral unit having a shape of a square pillar that is square in cross-section, with a one-side inclined surface thereof being inclined forwards, with the respective units being filled with stuffing, whereby the cervical vertebral support part and the occipital region support part form a normal sleep pillow that is used when a user sleeps while lying on his or her back.

A both-side inclined rectangular hexahedron unit having a shape of a rectangular pillar that is rectangular in cross-section and inclined at a both-side inclined surface thereof may be connected to an upper surface of the triangular pentahedron unit having the shape of the triangular prism that is triangular in cross-section and forming the cervical vertebral support part of the normal sleep pillow used when the user sleeps while lying on his or her back, and a one-side inclined square hexahedral unit having a shape of a square pillar that is square in cross-section and inclined at a one-side inclined surface that is connected to a rear surface of the both-side inclined rectangular hexahedron unit, thus forming a shoulder recess on a front surface of the pillow; and another one-side inclined square hexahedral unit, a rectangular hexahedron unit having a shape of a rectangular pillar that is rectangular in cross-section, and a triangular pentahedron unit may be horizontally connected to an upper portion of the occipital region support part of a back surface of the one-side inclined square hexahedral unit, thus further providing a sideways sleep pillow that is used when a user sleeps while lying on his or her side.

The normal sleep pillow and the sideways sleep pillow may be detachably attached to each other via detachment means.

The sideways sleep pillow may be provided on each of opposite sides of the normal sleep pillow.

Further, the present invention provides a pillow having a plurality of polygonal units, wherein a plurality of rhombic hexahedron units are connected to each other in a horizontal direction, each of the rhombic hexahedron units filled with stuffing and having a shape of a rhombic pillar that is rhombic in cross-section; and a plurality of isosceles-triangular pentahedron units each having a shape of an isosceles triangular prism that is isosceles triangular in cross-section, are connected to upper and lower portions of the plurality of rhombic hexahedron units in such a way so as to be in surface contact with each other, thus forming a shoulder recess on each of front and rear surfaces of the pillow, whereby a sideways sleep pillow used when a user sleeps with lying on his or her side is formed.

Further, the present invention provides a pillow having a plurality of polygonal units, including: a pair of rectangular panel-shaped hexahedron units filled with stuffing, stacked in two layers, having a shape of a rectangular pillar that is rectangular in cross-section while having a shape of a rectangular panel; a shoulder recess formed by stacking a one-side inclined square hexahedral unit, having a shape of a square pillar that is square in cross-section and inclined at a one-side inclined surface thereof, on front portions of upper surfaces of the pair of rectangular panel-shaped hexahedron units stacked in two layers; and another rectangular panel-shaped hexahedron unit connected to a rear surface of the one-side inclined square hexahedral unit in such a way so as to be connected in a horizontal direction, thus forming a sideways sleep pillow used when a user sleeps while lying on his or her side.

Any one of a pair of both-side inclined rectangular hexahedron units, the one-side inclined square hexahedral unit and the rectangular hexahedron unit may be selectively provided to be detachably attached to front and rear portions of an upper surface of the sideways sleep pillow via detachment means, thus having an ear-press prevention recess on a middle portion.

As described above, the pillow according to the present invention is advantageous in that it comprises a plurality of units, so that no deformation in shape on the whole occurs, thus keeping the head and the cervical vertebrae stable in the S shape and allowing the pillow to naturally come into close contact with the occipital region and the cervical vertebrae, therefore preventing the muscles from stiffening and the skeleton from being strained.

Further, the present invention is advantageous in that the pillow entirely comes into close contact with a region from the head to the cervical vertebrae and the shoulder, so that the load of the head is uniformly dispersed, thus allowing a user to have a comfortable deep sleep, preventing the neck from being deformed in a cervical hypolordosis shape, enabling the neck deformed in the cervical hypolordosis shape due to a bad living habit to be corrected to a normal cervical vertebrae S shape, and thereby correcting the cervical vertebrae.

Figure 1:
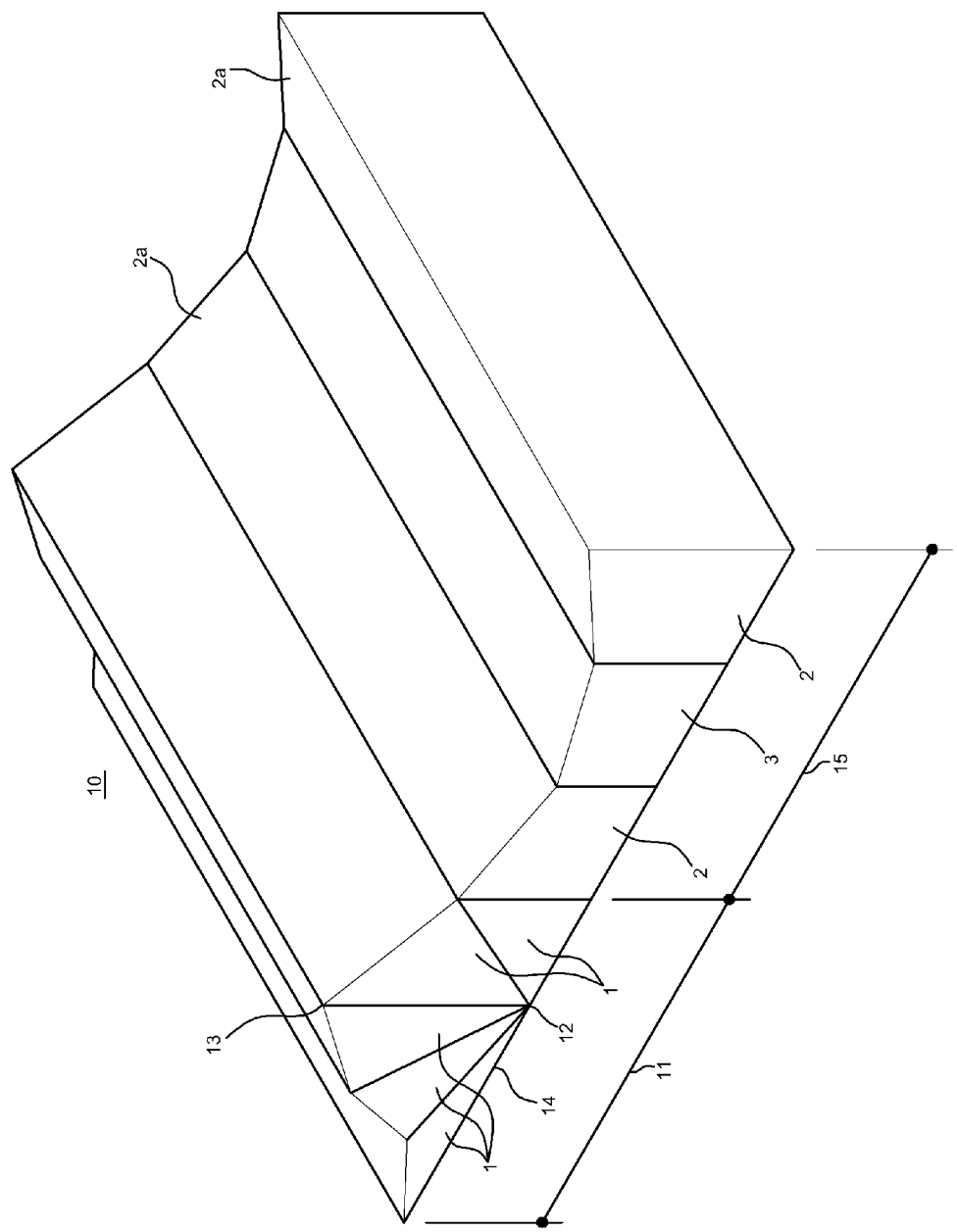
FIG. 1 is an entire perspective view showing a normal sleep pillow according to the present invention.

*Description of reference numerals of important parts*

1: triangular pentahedron unit
2: one-side inclined square hexahedral unit
3: rectangular hexahedron unit
4: both-side inclined rectangular hexahedron unit
5: rhombic hexahedron unit
6: isosceles-triangular pentahedron unit
7: rectangular panel-shaped hexahedron unit
10: normal sleep pillow
11: cervical-vertebral support part
12: bottom dead point part
13: upper dead point part        14: bottom part
15: occipital-region support part
20: sideways sleep pillow
21: shoulder recess              22: ear-press prevention recess
30: detachment means             100, 100': sideways sleep pillow
110: shoulder recess             120: ear-press prevention recess
M: corner end                    S: sewn line
P: stuffing                      C: pillow cover

DETAILED DESCRIPTION OF THE INVENTION

The preferred embodiments of the present invention will be described below in detail with reference to the accompanying drawings.

FIG. 1 shows a pillow according to an embodiment of the present invention, in which this pillow is used with a user's face facing upwards. In order to aid in understanding the present invention, the pillow that is used with the face facing upwards as described above, namely, used when a sleeper sleeps while lying on his or her back, will be referred to as a normal sleep pillow 10.

Figure 10:
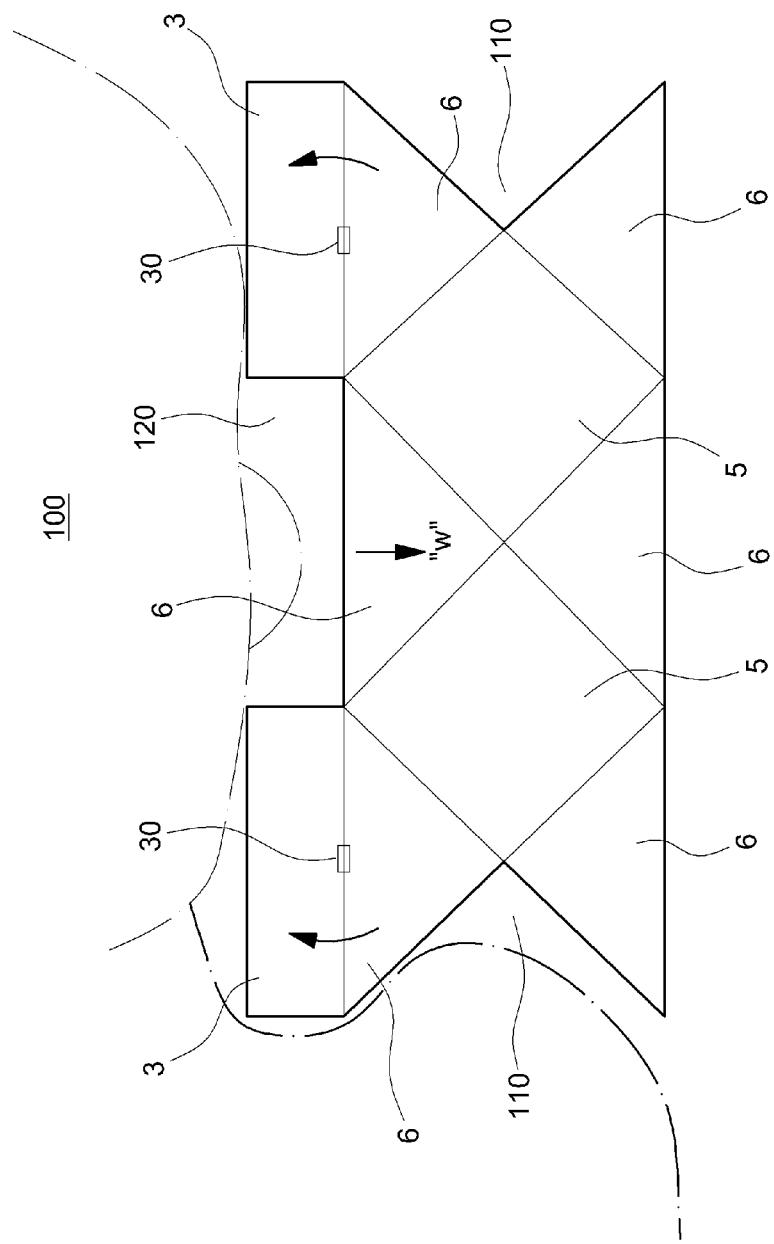
FIG. 10 is a side view showing an embodiment of a sideways sleep pillow of the present invention.

Thus, the pillow of the present invention is formed by sewing a triangular pentahedron unit 1, a one-side inclined square hexahedral unit 2 having a one-side inclined surface 2*a*, a rectangular hexahedron unit 3, a both-side inclined rectangular hexahedron unit 4 having a both-side inclined surface 4*a*, a rhombic hexahedron unit 5 and an isosceles-triangular pentahedron unit 6 shown in FIG. 10, and a rectangular panel-shaped hexahedron unit 7 shown in FIG. 12 together in such a way that they are in surface contact with and connected to each other, with the respective units filled with stuffing P.

Further, in these units, the triangular pentahedron unit 1 is shaped into a triangular prism which is triangular in cross-section, and the one-side inclined square hexahedral unit 2 is shaped into a square pillar which is square in cross-section and is formed in such a way that its one-side inclined surface 2*a* is inclined.

Furthermore, the rectangular hexahedron unit 3 is shaped into a rectangular pillar which is rectangular in cross-section, and the both-side inclined rectangular hexahedron unit 4 is shaped into a rectangular pillar which is rectangular in cross-section and is formed in such a way that its both-side inclined surface 4*a* is inclined.

Further, the rhombic hexahedron unit 5 is shaped into a rhombic pillar which is rhombic in cross-section, the isosceles-triangular pentahedron unit 6 is shaped into a isosceles triangular prism which is isosceles triangular in cross-section, and the rectangular panel-shaped hexahedron unit 7 is shaped into a rectangular pillar which is rectangular in cross-section and is formed in such a way so as to entirely have a shape of a rectangular panel.

Figure 2:
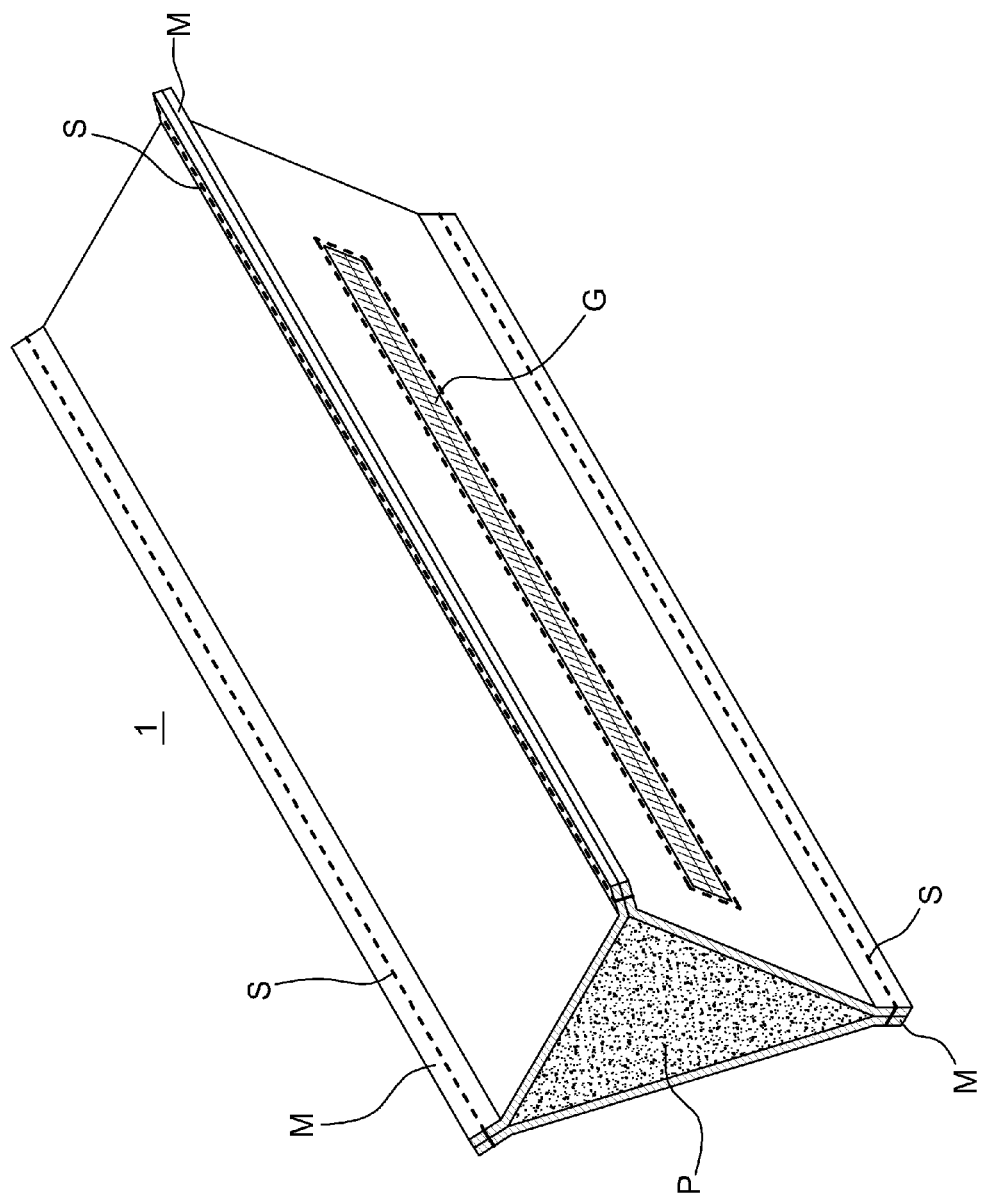
FIG. 2 is a partial sectional perspective view illustrating a unit according to the present invention.

Each unit is filled with the stuffing P similarly to the triangular pentahedron unit 1 illustrated in FIG. 2, and each corner end M is sewn to be sealed. Reference character S denotes a sewn line.

Moreover, each unit has a slide fastener G on a side thereof, to allow the stuffing P to be put therein by unfastening the slide fastener G.

Figure 3:
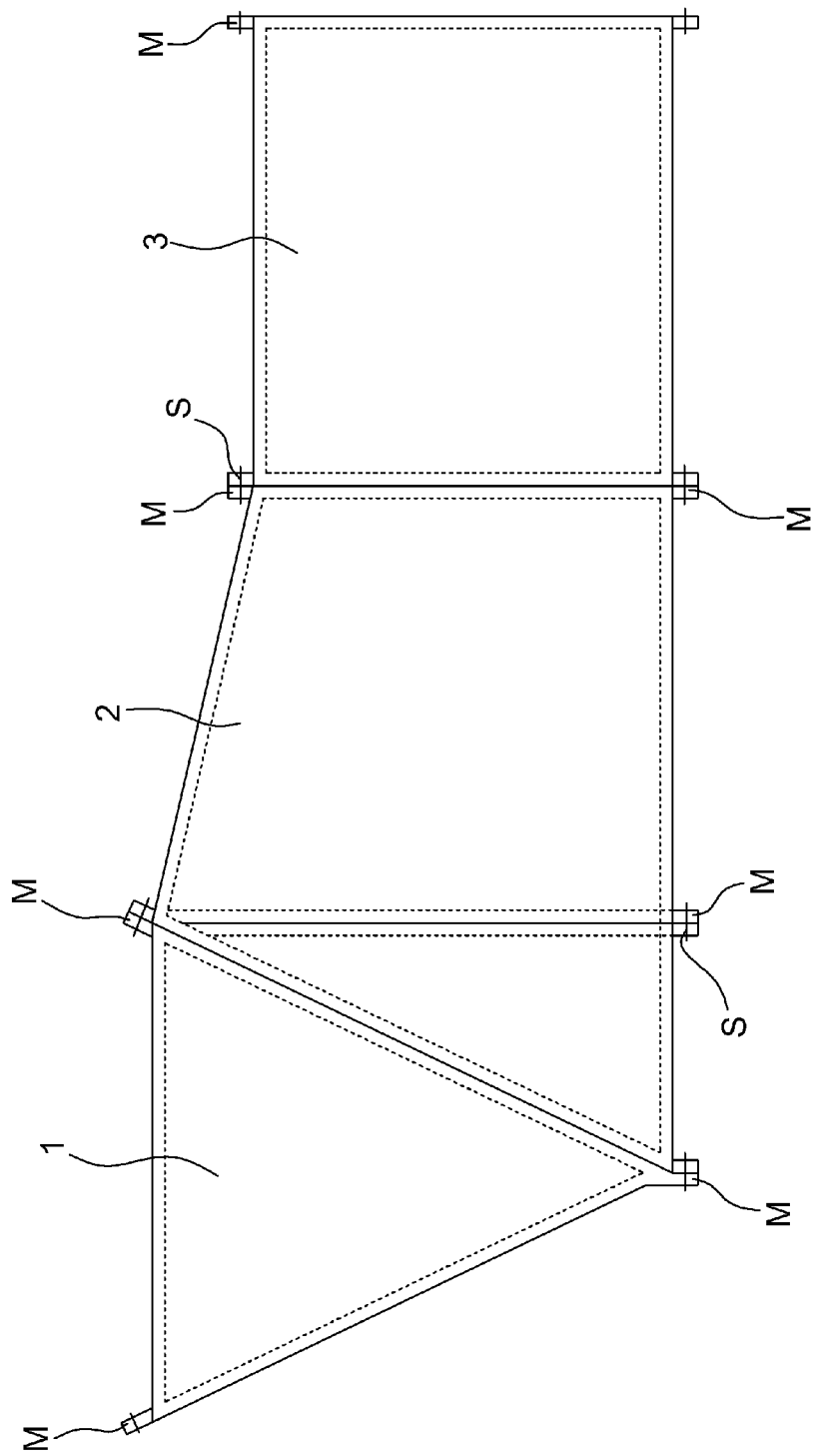
FIG. 3 is a view illustrating a connected state of units according to an embodiment of the present invention.
Figure 4:
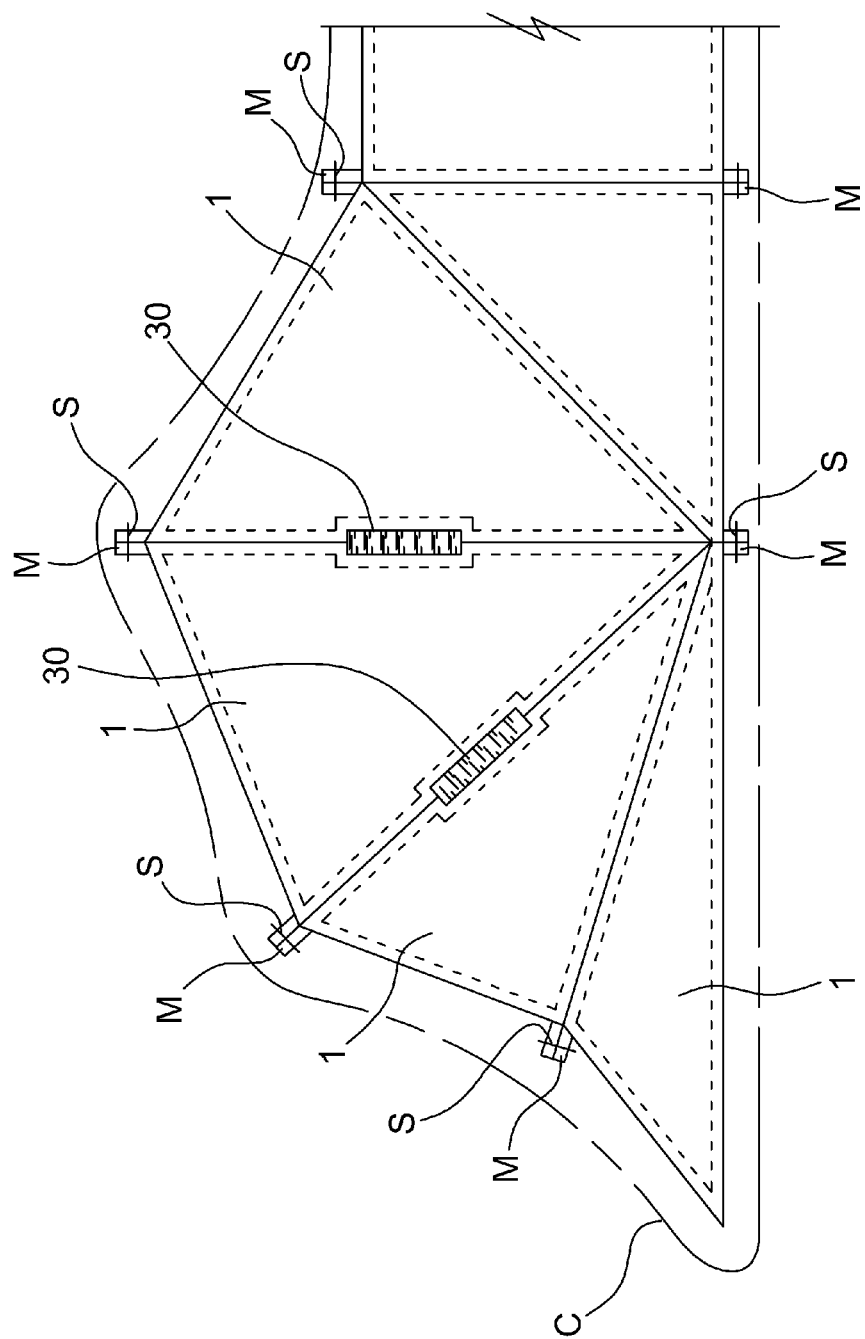
FIG. 4 is a view illustrating a connected state of units according to another embodiment of the present invention.

Thus, as shown in FIGS. 3 and 4, the units of the present invention come into surface contact with each other and then converge on corner ends M. In such a state, by sewing the corner ends, one pillow is obtained.

Further, as shown in FIG. 4, in order to make it easier to manufacture the pillow, a detachment means 30 such as magic tape is provided between the units according to circumstances. Thereby, the units which are to be connected in such a way so as to come into surface contact with each other are first attached to each other by the detachment means 30, and then the corner ends M of the corresponding units are sewn to be connected to each other.

Furthermore, the completed pillow is covered with a pillow cover C as shown by the imaginary line of FIG. 4, to conceal the corner ends M or the slide fastener G.

Thus, in order to aid in understanding the present invention, the corner end M or the slide fastener G provided on each unit will be omitted in some drawings, description and claims.

In the units of the present invention, for example, the triangular pentahedron unit 1 means a unit that is long and triangular when viewed from a side and has a total of five sides. The rectangular hexahedron unit 3 means a unit that is long and rectangular when viewed from a side and has a total of six sides. Other units mean units that have the shape conforming to designations thereof.

Thus, it is also possible to manufacture and implement the pillow of the present invention using other shapes of units that are not shown in the drawings.

Figure 5:
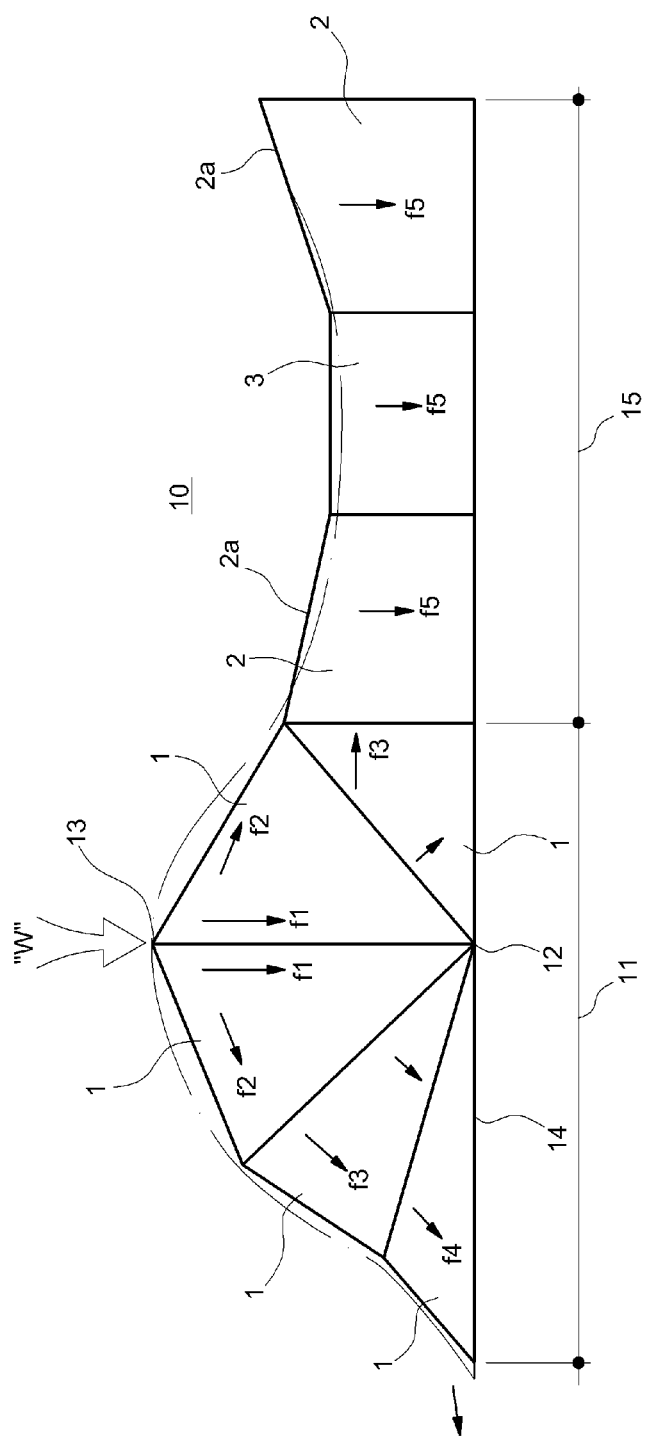
FIG. 5 is a side view illustrating the entire configuration and operation of the normal sleep pillow according to the present invention.

FIGS. 1 and 5 show the normal sleep pillow 10 according to an embodiment of the present invention.

The normal sleep pillow 10 has a cervical vertebral support part 11 on a front portion thereof and an occipital-region support part 15 on a rear portion thereof. Of course, the pillow having the cervical vertebral support part 11 and the occipital-region support part 15 is an already known technology.

However, according to the present invention, the cervical vertebral support part 11 has a bottom dead point part 12 formed by sewing gathered corner ends of a plurality of triangular pentahedron units 1.

Further, among the plurality of triangular pentahedron units 1, corner ends of a pair of triangular pentahedron units 1 located at a middle position are connected and sewn to each other, thus forming the upper dead point part 13.

Furthermore, a surface of one triangular pentahedron unit 1 protrudes to the front of a bottom part 14 in a wedge shape.

In addition, behind the cervical vertebral support part 11, one one-side inclined square hexahedral unit 2 whose one-side inclined surface 2a is inclined downwards to the rear, the rectangular hexahedron unit 3, and another one-side inclined square hexahedral unit 2 whose one-side inclined surface 2a is inclined downwards to the front are connected in a horizontal direction.

Figure 6:
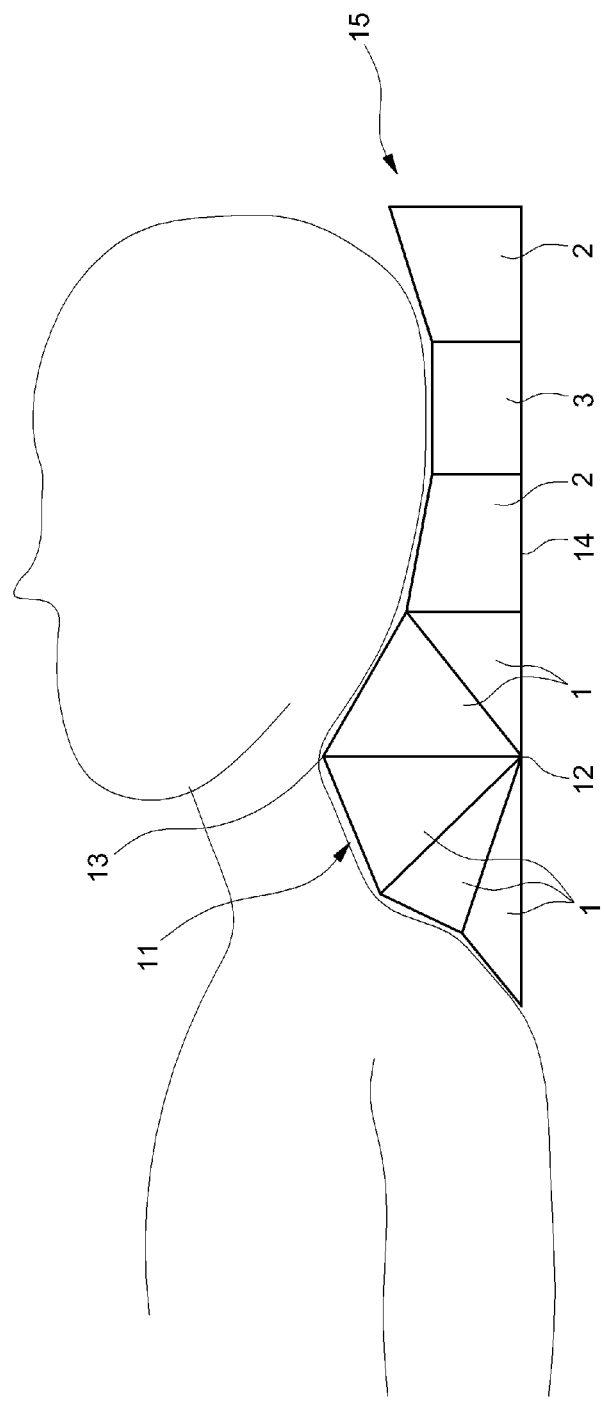
FIG. 6 is a side view showing the state before a user rests his or her head on the normal sleep pillow according to the present invention.

Thus, if the normal sleep pillow 10 is used as shown in FIG. 6, the occipital region is put on the occipital region support part 15, so that the cervical vertebrae is placed on the cervical vertebral support part 11. Thereby, the upper dead point part 13 protruding upwards is naturally pressed by a pressurized load W as shown in FIG. 5.

Therefore, the pressurized load W is first divided into the pair of triangular pentahedron units 1 to be dispersed, and is dispersed again into a vertical acting force F1 and a diagonal acting force F2, respectively, because the unit comprises the triangular pentahedron unit 1.

Further, the vertical acting force F1 and the diagonal acting force F2 act on, as a second acting force F3, another triangular pentahedron unit 1 which is provided on a lower portion in such a way so as to be in surface contact with the triangular pentahedron units. However, since the cervical vertebral support part comprises separate triangular pentahedron units 1, surface contact portions between the units are rarely deformed, but are subjected to only a pressurizing force with only the second acting force F3 transmitted thereto.

Thus, the pair of triangular pentahedron units 1 coupled to the upper dead point part 13 are held while surfaces of portions that are provided under the above triangular pentahedron units in such a way so as to be in surface contact therewith are rarely deformed. Hence, surfaces of upper portions that are not subjected to any acting force are pushed slightly outwards as shown by the imaginary line of FIG. 5. Consequently, the pillow naturally comes into close contact with the cervical vertebrae.

Further, among the triangular pentahedron units 1 that are subjected to the second acting force F3, the triangular pentahedron unit 1 located at a front position is pushed slightly outwards as shown by the imaginary line of FIG. 5, so that the pillow naturally comes into close contact with the cervical vertebrae.

However, among the triangular pentahedron units 1 that are subjected to the second acting force F3, the triangular pentahedron unit 1 located at a rear position is subjected to a much smaller acting force than the pressurized load W, because the second acting force F3 is dispersed in the vertical direction and the diagonal direction. Thus, among the triangular pentahedron units 1 that are subjected to the second acting force F3, the triangular pentahedron unit 1 located at the rear position is supported while being rarely deformed even if the triangular pentahedron unit 1 is subjected to the pressurized load W.

Further, among the triangular pentahedron units 1 that are subjected to the second acting force F3, the triangular pentahedron unit 1 disposed under the triangular pentahedron unit 1 located at the front portion is subjected to a third acting force F4 in a diagonal direction by the triangular pentahedron unit 1 located thereabove.

Therefore, a wedge-shaped protruding side of the triangular pentahedron unit 1 subjected to the third acting force F4 in the diagonal direction is pushed to the front as shown by the arrow of FIG. 5.

Figure 7:
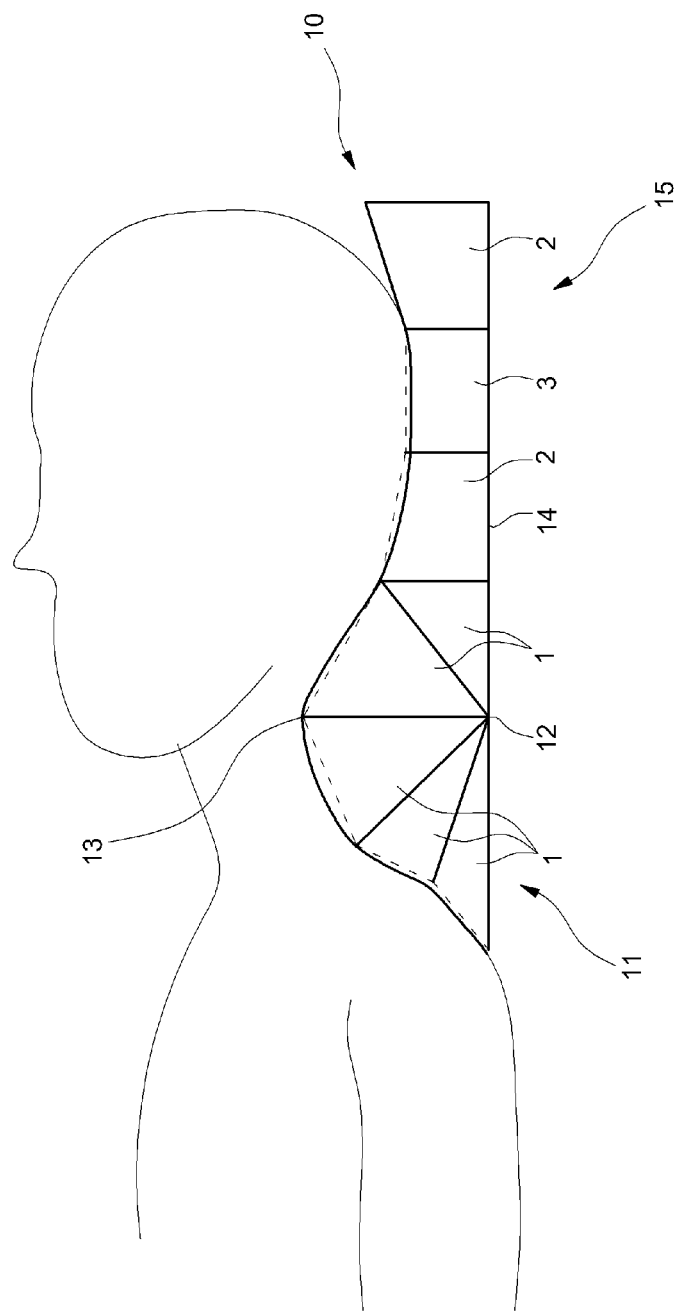
FIG. 7 is a side view showing the state when a user sleeps with his or her head resting on the normal sleep pillow according to the present invention.

Hence, as shown in FIG. 7, if the pressurized load W acts on the upper dead point part 13 of the cervical vertebral support part 11, the pressurized load W is dispersed and the triangular pentahedron units 1 naturally come into close contact with the cervical vertebrae and the shoulder. Further, since the triangular pentahedron units 1 comprise separate units, deformation in shape rarely occurs and thereby a stable state is maintained.

According to the present invention, the cervical vertebral support part 11 comprises a plurality of units, so that the pressurized load W is dispersed. In addition, among the triangular pentahedron units 1 that are subjected to the second acting force F3, the triangular pentahedron unit 1 disposed on the rear portion is supported while being rarely deformed even if the triangular pentahedron unit 1 is subjected to the pressurized load W. Thus, the occipital region support part 15 is rarely affected by the pressurized load W of the cervical vertebral support part 11.

Further, the occipital region support part 15 comprises a plurality of units, so that a pressurizing force generated by the load of the occipital region acting on the units merely acts as a linear acting force F5 in FIG. 5, but is rarely transmitted to the laterally connected units because they are laterally isolated from each other.

Therefore, the occipital region support part 15 is deformed while being slightly pressed by the load of the head as shown by the imaginary line of FIG. 5, so that the occipital region support part 15 naturally comes into close contact with the occipital region.

In other words, since the pillow according to the present invention comprises a plurality of units, the entire shape of the pillow is not changed, and thus the head and the cervical vertebrae are kept stable in the S shape. Hence, the cervical vertebral support part 11 and the occipital region support part 15 come into close contact with the occipital region and the cervical vertebrae, thus preventing the muscles from stiffening and the skeleton from being stained.

Further, the pillow entirely comes into close contact with a region from the head to the cervical vertebrae and the shoulder, and besides, the load of the head is uniformly dispersed, thus helping a user have a comfortable deep sleep, and preventing the neck from being deformed in a cervical hypolordosis shape, and correcting the neck deformed in the cervical hypolordosis shape due to a bad living habit to the normal cervical vertebrae in the S shape.

Figure 8:
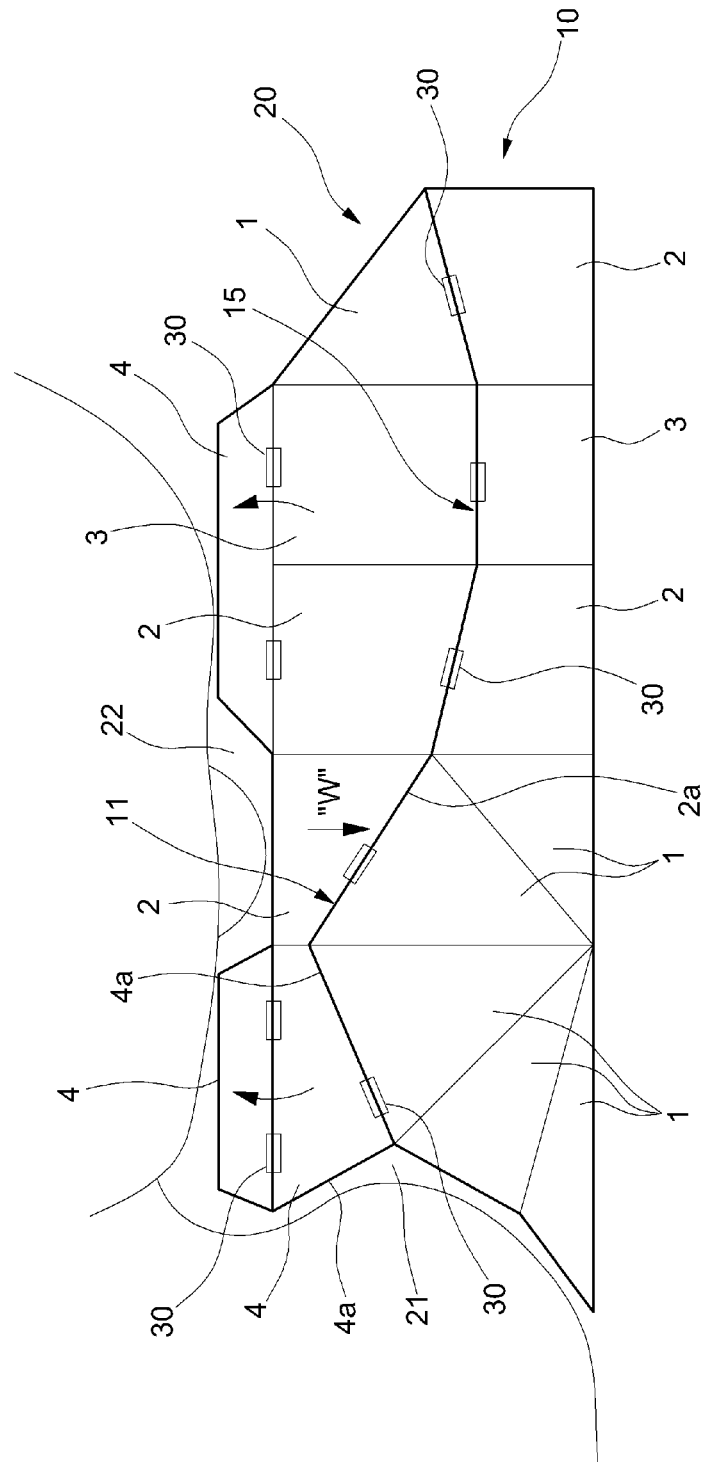
FIG. 8 is a side view showing the state in which a sideways sleep pillow is adapted to the normal sleep pillow of the present invention.

FIG. 8 shows another embodiment according to the present invention.

This embodiment further includes a pillow which is provided on the normal sleep pillow 10 to be used when lying on a user's side.

Further, the pillow used when lying on a user's side is used when sleeping on his or her side, and hereinafter will be referred to as a sideways sleep pillow 20.

Referring to FIG. 8, in front of an upper surface of the cervical vertebral support part 11 of the normal sleep pillow 10, a both-side inclined rectangular hexahedron unit 4 having a both-side inclined surface 4a and a one-side inclined square hexahedral unit 2 having a one-side inclined surface 2a are connected to form a shoulder recess 21.

Further, on the occipital region support part 15 behind the one-side inclined square hexahedral unit 2, the one-side inclined square hexahedral unit 2, the rectangular hexahedron unit 3 and the triangular pentahedron unit 1 are connected in a horizontal direction.

Furthermore, the normal sleep pillow 10 and the sideways sleep pillow 20 may be detachably coupled to each other via the detachment means 30.

The detachment means 30 is preferably magic tape. However, it is possible to use a slide fastener according to circumstances.

Figure 9:
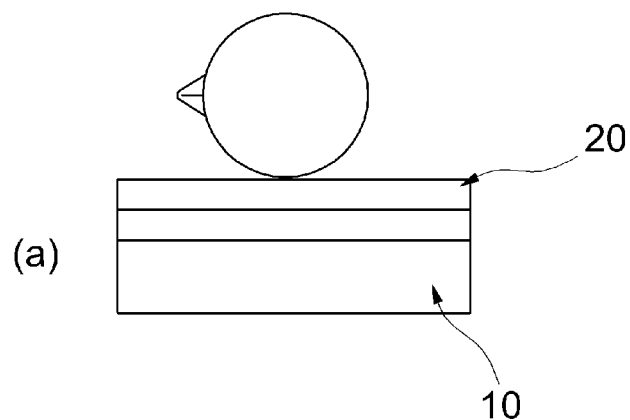
FIGS. 9(*a*) and 9(*b*) are views showing an embodiment of the state in which the sideways sleep pillow of the present invention is adopted.
Figure 9:
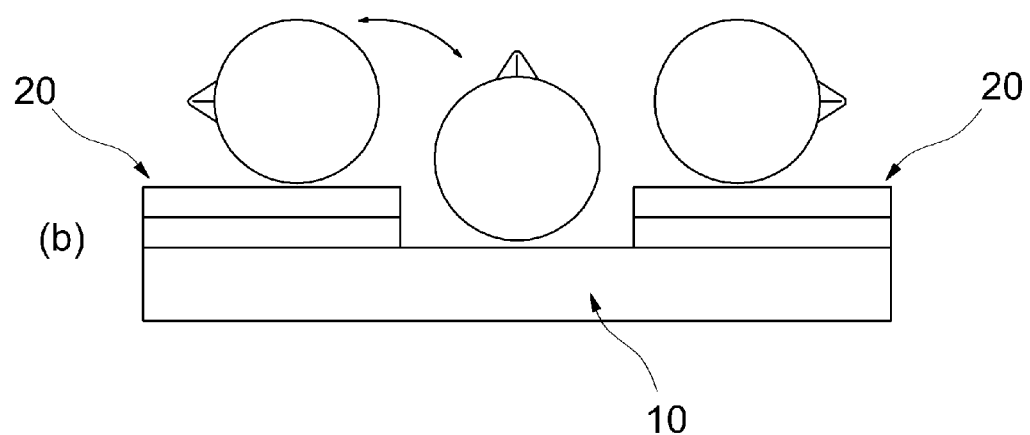

Further, as shown in FIG. 9(a), the sideways sleep pillow 20 may be provided throughout an entire upper portion of the normal sleep pillow 10. Meanwhile, as shown in FIG. 9(b), the sideways sleep pillow 20 may be provided on both sides of the normal sleep pillow 10, respectively. Thus, when a user sleeps on his or her back, he or she uses the normal sleep pillow 10. In contrast, when he or she sleeps on his or her side, he or she uses the sideways sleep pillow 20.

Turning back to FIG. 8, the present invention may have a pair of both-side inclined rectangular hexahedron units 4 on front and rear portions of the upper surface of the sideways sleep pillow 20, respectively, in such a way so as to be detachably attached by the detachment means 30, thus forming an ear-press prevention recess 22 on a middle portion.

Thus, since the pillow of the present invention increases in height due to the sideways sleep pillow 20, the shoulder is inserted into the shoulder recess 21 to come into close contact with the pillow when a user lies on his or her side as shown by the imaginary line of FIG. 8.

Therefore, the head is stably placed on the sideways sleep pillow 20, and the pressurized load W acts on the middle portion, so that front and rear ends are relatively slightly raised up. As a result, the sideways sleep pillow 20 naturally comes into close contact with the head and the cervical vertebrae.

Further, the sideways sleep pillow 20 comprises a plurality of units, so that the load of the head is dispersed and the shape of the pillow is rarely changed. Since the sideways sleep pillow is the same as the normal sleep pillow 10, a detailed description thereof will be omitted herein.

Figure 11:
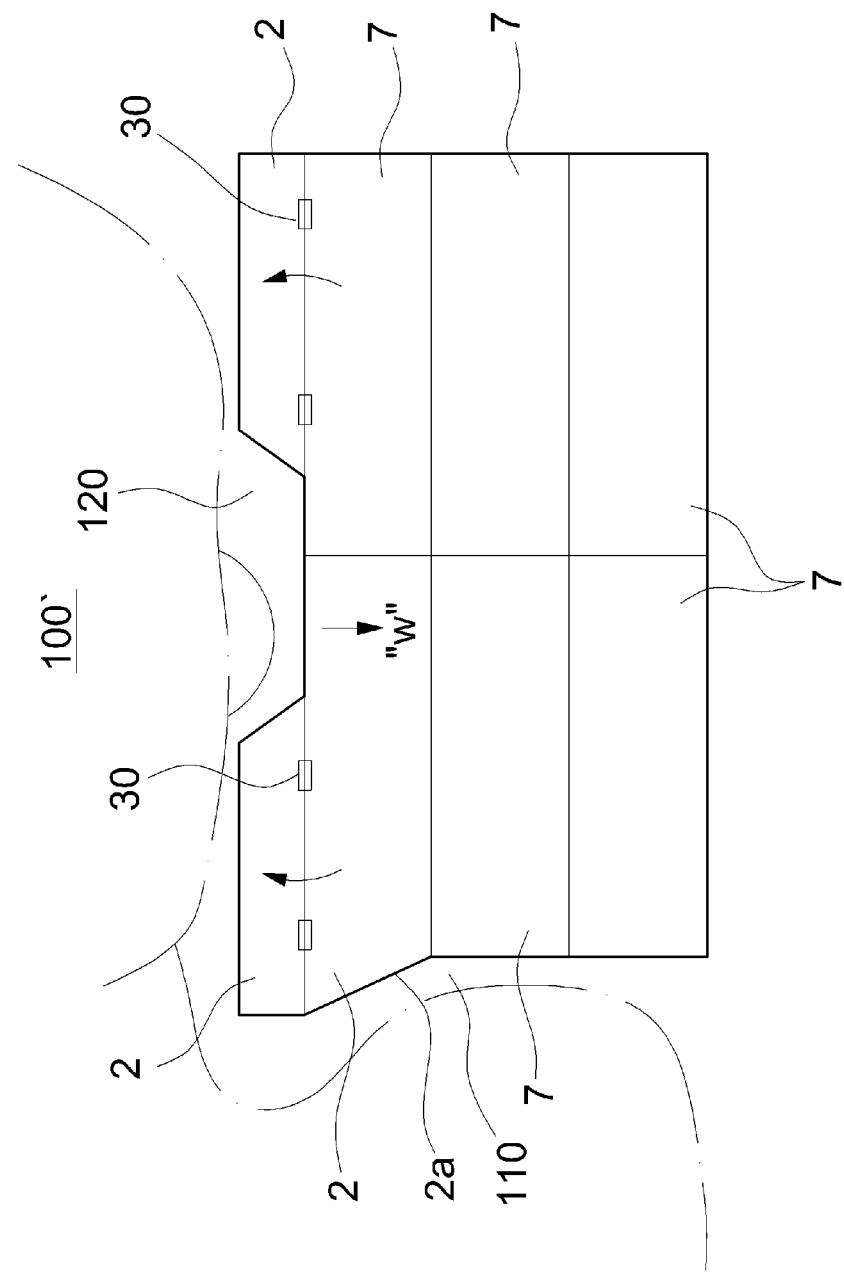
FIG. 11 is a side view showing another embodiment of a sideways sleep pillow of the present invention.

FIGS. 10 and 11 illustrate a pillow used only when lying on a user's side. In order to aid in understanding the present invention, the pillow will be referred to as a sideways sleep pillow 100, 100'.

FIG. 10 shows a sideways sleep pillow 100 according to an embodiment.

The sideways sleep pillow 100 is formed by horizontally connecting a plurality of rhombic hexahedron units 5 to each other. A plurality of isosceles-triangular pentahedron units 6 are provided on upper and lower portions of the plurality of rhombic hexahedron units 5 in such a way so as to be in surface contact therewith. Shoulder recesses 110 are provided, respectively, on front and rear sides of the pillow.

Further, a pair of rectangular hexahedron units 3 is provided on front and rear portions of the upper surface of the sideways sleep pillow 100, respectively, to be detachably attached via detachment means 30, thus forming an ear-press prevention recess 120 on a middle portion.

Thus, if the sideways sleep pillow 100 of the present invention is used when lying on a user's side as shown by the imaginary line of FIG. 10, the shoulder is inserted into the shoulder recess 110 to be in close contact therewith.

Hence, the head is stably placed on the sideways sleep pillow 100, and the pressurized load W acts on the middle portion so that front and rear ends are relatively slightly raised up, as shown by the arrow. As a result, the sideways sleep pillow 100 naturally comes into close contact with the head and the cervical vertebrae.

Further, the sideways sleep pillow 100 comprises a plurality of units, so that the load of the head is dispersed and the shape of the pillow is rarely changed. Since this is the same as the normal sleep pillow 10, a detailed description thereof will be omitted herein.

FIG. 11 shows a sideways sleep pillow 100' according to another embodiment.

The sideways sleep pillow 100' of this embodiment includes a pair of rectangular panel-shaped hexahedron units 7 that are connected to each other in such a way so as to be stacked in two layers.

Further, in front of upper surfaces of the pair of rectangular panel-shaped hexahedron units 7 that are stacked in two layers, the one-side inclined square hexahedral unit 2 whose one-side inclined surface 2a is inclined downwards is stacked to be connected, thus forming the shoulder recess 110.

Furthermore, another rectangular panel-shaped hexahedron unit 7 is horizontally connected to the rear portion of the one-side inclined square hexahedral unit 2.

Further, a pair of one-side inclined square hexahedral units 2 is provided on front and rear portions of the upper surface of the sideways sleep pillow 100', respectively, to be detachably attached via detachment means 30, thus forming an ear-press prevention recess 120 on a middle portion.

Thus, if the sideways sleep pillow 100' is used when lying on a user's side as shown by the imaginary line of FIG. 11, the shoulder is inserted into the shoulder recess 110 to be in close contact therewith.

Hence, the head is stably placed on the sideways sleep pillow 100', and the pressurized load W acts on the middle portion, so that front and rear ends are relatively slightly raised up, as shown by the arrow. As a result, the sideways sleep pillow 100' naturally comes into close contact with the head and the cervical vertebrae.

Further, the sideways sleep pillow 100' is formed by stacking a plurality of units up, so that the load of the head is dispersed and the shape of the pillow is rarely changed. Since this is the same as the normal sleep pillow 10, a detailed description thereof will be omitted herein.

Therefore, the sideways sleep pillow 100, 100' of the present invention comprises a plurality of units, so that no deformation in shape on the whole occurs, thus keeping the head and the cervical vertebrae stable, therefore preventing the muscles from stiffening and the skeleton from being strained even if a user sleeps on his or her side.

Further, the pillow entirely comes into close contact with a region from the head to the cervical vertebrae and the shoulder, so that the load of the head is uniformly dispersed, thus allowing a user to have a comfortable deep sleep.

Although the embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A pillow having a plurality of polygonal units, comprising:
 a central normal sleep pillow portion comprising:
 a plurality of triangular pentahedron units, each of which having a shape of a triangular prism that is triangular in cross-section, so that the plurality of triangular pentahedron units are configured to provide a cervical vertebral part;

two one-side inclined square hexahedral units, each of which having a shape of a square pillar that is square in cross-section, with a one-side inclined surface thereof being inclined; and a rectangular hexahedron unit having a shape of a rectangular pillar that is rectangular in cross-section and disposed between the two one-side inclined square hexahedral units, so that the two one side inclined square hexahedral units and the rectangular hexahedron unit are configured to provide an occipital-region support part; and two sideways pillow portions, one disposed on each side of the central normal sleep pillow portion, wherein each of the two sideways pillow portions comprises:

a first plurality of isosceles-triangular pentahedron units, each of which having a shape of an isosceles triangular prism that is isosceles triangular in cross-section, wherein the first plurality of isosceles-triangular pentahedron units are disposed on a same plane as a bottom surface of the central normal sleep pillow portion;

a plurality of rhombic hexahedron units, each of which having a shape of a rhombic pillar that is rhombic in cross-section, wherein the plurality of rhombic hexahedron units are stacked on the plurality of isosceles-triangular pentahedron units;

a second plurality of isosceles-triangular pentahedron units, each of which having a shape of an isosceles triangular prism that is isosceles triangular in cross-section, wherein the second plurality of isosceles-triangular pentahedron units are disposed on an elevated plane parallel to the bottom surface of the central normal sleep pillow portion; and two rectangular hexahedron units, each of which having a shape of a rectangular pillar that is rectangular in cross-section and disposed on the second plurality of isosceles-triangular pentahedron units, so that the two rectangular hexahedron units are configured to provide an ear-press prevention recess, whereby the units are sewn together in such a way so as to selectively come into surface contact with each other or be stacked, thus forming one pillow, with the respective units being filled with stuffing.

2. A pillow having a plurality of polygonal units, comprising:

a cervical vertebral support part configured to support a cervical region of a user, comprising:

a bottom dead point part formed by sewing gathered lower corner ends of a plurality of triangular pentahedron units, each of the triangular pentahedron units being filled with stuffing and having a shape of a triangular prism that is triangular in cross-section;

an upper dead point part formed by connecting and sewing upper corner ends of a pair of triangular pentahedron units disposed on a middle portion among the plurality of triangular pentahedron units; and a surface of one triangular pentahedron unit protruding to a front of a bottom part, in a wedge shape; and an occipital region support part connected to a rear portion of the cervical vertebral support part, configured to support an occipital region of said user, and formed by horizontally connecting the following units:

two one-side inclined square hexahedral units, each of which having a shape of a square pillar that is square in cross-section, with a one-side inclined surface thereof being inclined backwards and disposed between the two one-side inclined square hexahedral units;

a rectangular hexahedron unit having a shape of a rectangular pillar that is rectangular in cross-section;

another one-side inclined square hexahedral unit having a shape of a square pillar that is square in cross-section, with a one-side inclined surface thereof being inclined forwards, with the respective units being filled with stuffing, whereby the cervical vertebral support part and the occipital region support part form a normal sleep pillow that is used when a user sleeps while lying on his or her back.

3. The pillow according to claim 2, wherein a both-side inclined rectangular hexahedron unit having a shape of a rectangular pillar that is rectangular in cross-section and inclined at a both-side inclined surface thereof is connected to an upper surface of the triangular pentahedron unit having the shape of the triangular prism that is triangular in cross-section and forming the cervical vertebral support part of the normal sleep pillow used when the user sleeps while lying on his or her back, and a one-side inclined square hexahedral unit having a shape of a square pillar that is square in cross-section and inclined at a one-side inclined surface that is connected to a rear surface of the both-side inclined rectangular hexahedron unit, thus forming a shoulder recess on a front surface of the pillow; and another one-side inclined square hexahedral unit, a rectangular hexahedron unit having a shape of a rectangular pillar that is rectangular in cross-section, and a triangular pentahedron unit are horizontally connected to an upper portion of the occipital region support part of a back surface of the one-side inclined square hexahedral unit, thus further providing a sideways sleep pillow that is used when a user sleeps while lying on his or her side.

4. The pillow according to claim 3, wherein the normal sleep pillow and the sideways sleep pillow are detachably attached to each other via detachment means.

5. The pillow according to claim 3, wherein the sideways sleep pillow is provided on each of opposite sides of the normal sleep pillow.

6. The pillow according to claim 3, wherein any one of a pair of both-side inclined rectangular hexahedron units, the one-side inclined square hexahedral unit and the rectangular hexahedron unit is selectively provided to be detachably attached to front and rear portions of an upper surface of the sideways sleep pillow via detachment means, thus having an ear-press prevention recess on a middle portion.

* * * * *